United States Patent [19]

Jones

[11] Patent Number: 4,561,289

[45] Date of Patent: Dec. 31, 1985

[54] PERFORATED END PLUG PLATE FOR TESTING CORE SAMPLES

[75] Inventor: Stanley C. Jones, Littleton, Colo.

[73] Assignee: Marathon Oil Company, Findlay, Ohio

[21] Appl. No.: 651,561

[22] Filed: Sep. 14, 1984

[51] Int. Cl.⁴ .............................................. G01N 15/08
[52] U.S. Cl. ....................................................... 73/38
[58] Field of Search ............................................ 73/38

[56] References Cited

U.S. PATENT DOCUMENTS

| | | | |
|---|---|---|---|
| 966,078 | 8/1910 | Bowman | 73/38 |
| 2,516,188 | 6/1950 | Dietert et al. | 73/38 |
| 2,539,355 | 1/1951 | Reichertz | 73/38 |
| 2,618,151 | 11/1952 | Leas | 73/38 |
| 2,646,678 | 7/1953 | Standing et al. | 73/38 X |
| 2,676,485 | 4/1954 | Morgan | 73/38 |
| 2,737,804 | 3/1956 | Herzog et al. | 73/38 |
| 2,745,057 | 5/1956 | Dotson . | |
| 2,842,958 | 7/1958 | Sayre, Jr. et al. | 73/38 |
| 3,158,020 | 12/1964 | Donaldson | 73/38 |
| 3,199,341 | 8/1965 | Heuer, Jr. et al. . | |
| 3,466,925 | 9/1969 | Ziegenhagen et al. | 73/38 |
| 3,577,767 | 5/1971 | Stedile | 73/38 |
| 3,839,899 | 10/1974 | McMillen | 73/38 |
| 4,043,407 | 8/1977 | Wilkins . | |
| 4,052,885 | 10/1977 | Shuck | 73/38 |
| 4,083,228 | 4/1978 | Turner | 73/32 R |
| 4,227,397 | 10/1980 | Neri | 73/38 |
| 4,253,327 | 3/1981 | Wiley | 73/38 |
| 4,287,754 | 9/1981 | Heitmann | 73/38 |
| 4,403,501 | 9/1983 | Pezzi | 73/38 |
| 4,430,890 | 2/1984 | Hains | 73/147 |
| 4,454,095 | 6/1984 | Holt | 422/64 |

FOREIGN PATENT DOCUMENTS 1268577  6/1961  France .................. 73/38

OTHER PUBLICATIONS

"A Rapid Accurate Unsteady-State Klinkenberg Permeameter", Stanley C. Jones, Marathon Oil Co., Littleton, CO, Oct. 1972.

*Primary Examiner*—S. Clement Swisher
*Assistant Examiner*—Joseph W. Roskos
*Attorney, Agent, or Firm*—Jack L. Hummel; Rodney F. Brown

[57] ABSTRACT

Improved perforated end plug circular plates for abutting core samples during porosity and permeability testing. The perforated end plug plates having at least one circular channel formed on the surface opposing the abutting surface of the plate, a plurality of radial channels formed also on the opposing surface and being in fluid communication with the circular channel. At least one circular array of holes formed in the surface abutting the core sample and in fluid communication with the circular and radial channels on the opposing surface.

6 Claims, 5 Drawing Figures

PERFORATED END PLUG PLATE FOR TESTING CORE SAMPLES

BACKGROUND OF THE ART

1. Related Application

This application is related to "Apparatus and Method for the Automatic Porosity and Permeability Testing of Multiple Core Samples", Ser. No. 651,558, filed concurrently with this application.

2. Field of the Invention

The present invention relates to a plate design which is placed at opposing ends of core samples obtained from an underlying rock formation when conducting tests on the cores such as ascertaining permeability and porosity of the cores.

3. Background of the Art

Two important parameters for evaluating production of an underlying oil or gas bearing formation are to determine the permeability and porosity of core samples taken from the formation. A measurement of permeability of the core provides an indication as to how fast the oil or gas will flow from the formation upon production whereas a measurement porosity provides information as to the amount of oil or gas contained within the formation. In conducting such tests on core samples, especially when overburden pressures are applied to the core samples, perforated end plug plates are used on each end of the sample to aid in the distribution of gas into the sample.

The determination of both porosity and permeability are based upon complex mathematical determinations and both are common measurements in the oil and gas industry. An understanding of these mathematical formulas is not necessary for the understanding of the present invention. However, a discussion of the mathematical formulas for determining Klinkenberg permeability, the Klinkenberg slip factor and the Forcheimer turbulence factor observed in core plugs is set forth in the inventor's prior publication entitled "A Rapid Accurate Unsteady-State Klinkenberg Permeameter", *Society of Petroleum Engineers Journal*, October, 1972, Pages 383-397. In that publication, a method and apparatus for performing permeability tests on core samples is set forth. In that disclosure, each sample core is manually loaded into a Hassler core holder and the sleeve contained therein is then pressurized to simulate an overburden pressure. A gas, such as nitrogen, is then introduced through an end plate having circular formed holes into one end of the core and the passage of the gas through the core into a second end plate is then determined to ascertain the permeability. End plug plates are utilized at opposing ends of the core sample to aid in the distribution of gas and to provide structural support to the core sample.

In addition, prior to the filling of this invention, a patentability search was conducted on the above identified related application which uncovered the following patents:

| Inventor | Reg. No. | Reg. Date |
|---|---|---|
| Bowman | 966,078 | Aug. 2, 1910 |
| Dietert et al. | 2,516,188 | July 25, 1950 |
| Reichertz | 2,539,355 | Jan. 23, 1951 |
| Leas | 2,618,151 | Nov. 18, 1952 |
| Herzog et al. | 2,737,804 | Mar. 13, 1956 |
| Dotson | 2,745,057 | May 8, 1956 |

-continued

| Inventor | Reg. No. | Reg. Date |
|---|---|---|
| Donaldson | 3,158,020 | Nov. 24, 1964 |
| Heuer, Jr. et al. | 3,199,341 | Aug. 10, 1965 |
| McMillen | 3,839,899 | Oct. 8, 1974 |
| Wilkins | 4,043,407 | Aug. 23, 1977 |
| Turner et al. | 4,083,228 | Apr. 11, 1978 |
| Neri | 4,227,397 | Oct. 14, 1980 |
| Wiley | 4,253,327 | Mar. 3, 1981 |
| Heitmann et al. | 4,287,754 | Sept. 8, 1981 |
| Pezzi | 4,403,501 | Sept. 13, 1983 |
| Hains | 4,430,890 | Feb. 14, 1984 |
| Holt | 4,454,095 | June 12, 1984 |

Only the following discussed patents disclosed types of perforated end plugs.

The Wiley patent sets forth a method and apparatus for measuring core permeability at overburden conditions of both pressure and temperature. Each core must be manually loaded into a sleeve having end plugs inserted into the sleeve. Then the entire assembly is placed into a hydrostatic cell wherein hydraulic fluid is pressurized around the end plugs and the sleeve to simulate the overburden pressure. The fluid is then injected through one end plug, through a sintered plate, through the core, out a second sintered plate and through the opposing end plug.

In Leas, a manually loaded cell for measuring relative permeability is disclosed wherein a flexible elastic sleeve selectively pressurizes the sides of the core during testing so as to simulate overburden stress. Fluids are injected into the end of the core to measure the permeability of the core. To insert or remove the core, a vacuum is pulled around the elastic sleeve so that the core can be manually removed or inserted. Porous disks are placed on each end of the core to aid in the distribution of the fluid to and from the core. The porous disks of Leas have two embodiments. The first embodiment has a rectangular grid of channels on the side of the plate abutting the core sample and the second embodiment provides a shallow cylindrical cavity. The cavity and grooves both are in fluid communication with a center hole. The opposite side of each plate is flat.

Heuer, Jr. et al. discloses a method and apparatus for measuring compressibility of core samples by encapsulating the core sample in a fluid-impervious sheet such as flexible plastic and then suspending the core sample in a pressure vessel and subjecting the sample to high pressure while passing fluids to and from opposing ends of the core sample through fluid-permeable steel disks.

The Morgan patent sets forth a method of sealing cores while determining the permeability of the core by providing a counter-pressure environment around the core with an atmosphere of non-wetting fluid. The pressure eliminates the use of sealing material such as pitch, tar, or a separate sealing medium such as plastic or rubber. A capillary diaphragm is used on opposing ends of the core sample.

A disadvantage with prior art approaches as found in the Leas "waffle" design occurs when the applied stresses cause the plate to deform (imprint) the ends of the core. This not only may damage the core, but also blocks the gas passageways in the plate possibly effectuating a less than uniform distribution of gas in the core. Non-uniform distribution of gas may cause errors to occur in the permeability or porosity readings.

None of the above discussed patents set forth an end plug plate design of the present invention which includes an array of fluid passage channels on one side of the plate and an array of circular holes on the other side for uniform distribution of gas into the core sample while minimizing damage to the core samples when an overburden stress is placed thereon.

SUMMARY OF THE INVENTION

To solve the problem of maximizing uniform gas flow distribution into core samples subject to overburden stresses when conducting tests such as permeability and porosity tests while also minimizing damage to the physical ends of each core, the perforated end plugs of the present invention include a first array of radial and circular channels in fluid communication with the delivery of fluids such as gas into the tester and a second array of circular holes in fluid communication with said channels located on the surface abutting the end of the core sample.

DETAILED DESCRIPTION

Figure 1:
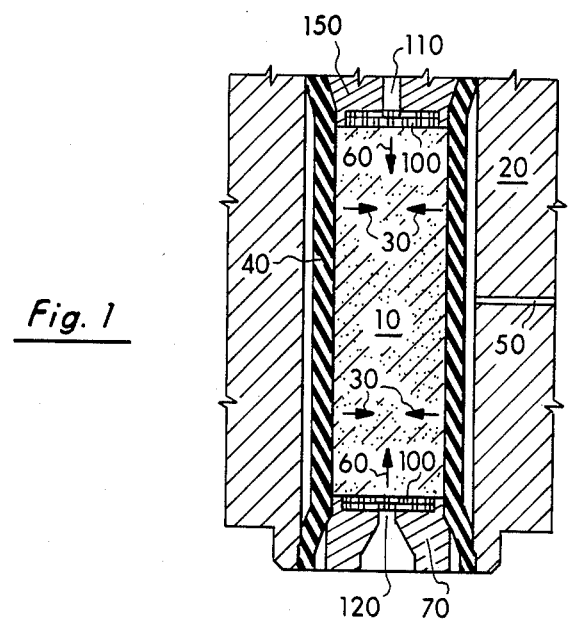
FIG. 1 is a cross-sectional view of the perforated base plate of the present invention engaging the upper and lower ends of a core sample under stress in a test chamber.

In FIG. 1 is shown a core sample 10 being held in a test chamber 20 wherein radial forces 30 are being applied by an elastic sleeve 40 by means of pressurized fluid flowing in passageway 50. In addition, the core 10 has an axial stress 60 being applied to the ends of the core sample 10 by means of a piston 70. The application of the radial forces 30 and the axial forces 60 are taught in accordance with the teaching set forth in the above identified co-pending application.

The present invention 100 relates to the design of a perforated end plug plate which is placed on opposing ends of the core sample 10 and which functions to extend fluids, such as gas, into and from the core sample 10. The gas is delivered through passageway 110 and out through passageway 120 when conducting a permeability test. The present invention could be used with fluids other than helium gas and can be used in other types of tests such as electrical resistivity tests.

Figure 2:
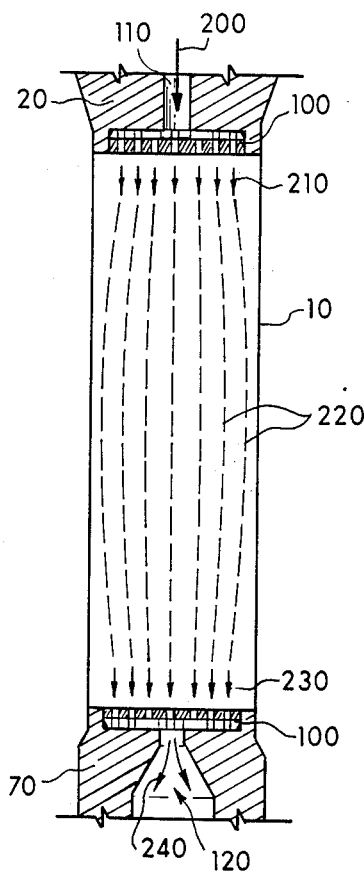
FIG. 2 is an illustration showing the uniform distribution of gas being extended through the base plates to and from the core sample.

This is more graphically shown in FIG. 2 wherein helium gas 200 is delivered through upper passageway 110 to the upper perforated end plug plate 100 through the plate 100 into the upper end of the core 10. As can be witnessed, the function of the upper face plate 100 is to distribute uniformly, as shown by arrows 210, the incoming helium gas over the top surface of the core sample 10. The gas 210 is evenly distributed throughout the sample core 10 as shown by dotted lines 220 and is uniformly collected as shown by arrows 230 by the lower perforated face plate 100 for delivery out from the core sample 10 as shown by arrows 240. The distribution of gas is uniform despite the application of the axial overburden stress to the core sample 10.

Figure 4:
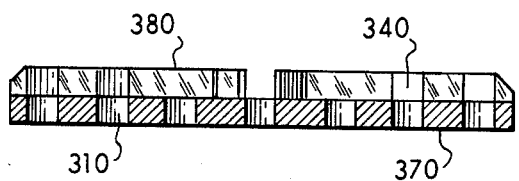
FIG. 4 is a cut-away view of the perforated base plate along lines 4—4.
Figure 3:
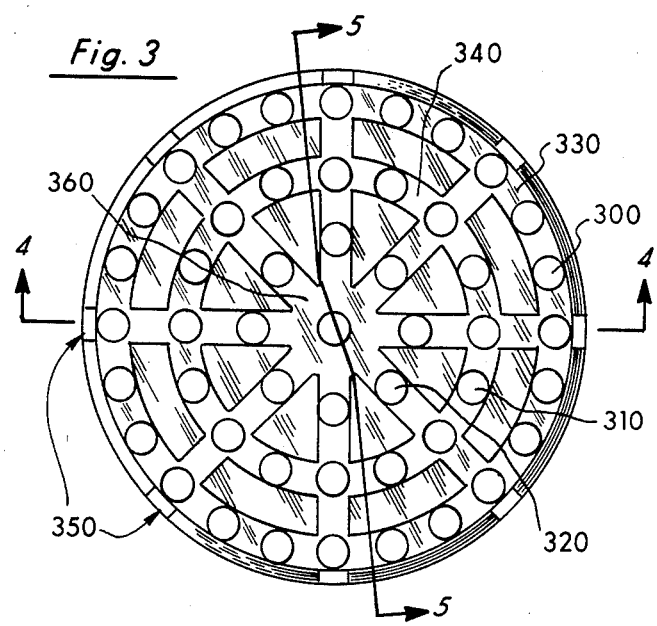
FIG. 3 is a top planar view of the perforated base plate of the present invention.
Figure 5:
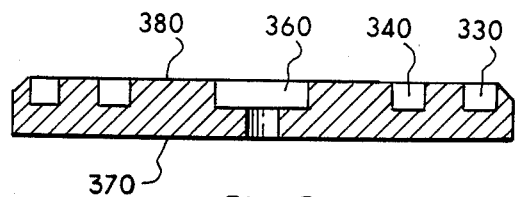
FIG. 5 is a cut-away view of the perforated base plate of FIG. 3 along lines 5—5.

The details of the perforated plate 100 of the present invention are shown in FIGS. 3-5. The perforated plate 100 is cylindrically shaped and has, in the preferred embodiment, three circular arrangements of formed circular holes 300, 310, and 320. The diameter of the plate is such to be used with cores of, for example, one inch diameter. The first circular arrangement of twenty-four holes 300 is oriented to correspond with a first circular channel 330 and the second circular row of sixteen formed holes 310 is disposed in a second formed circular channel 340. A plurality of outwardly directed radial channels 350 is directed from an inner formed circular passageway 360. The third circular row of eight formed holes 320 is disposed only in the outwardly directed radial channels 350.

Hence, as shown in FIG. 3, the downward surface 370, as set forth in FIGS. 1 and 2, only has the exposed circular arrangement of formed holes 300, 310, 320 showing an abutting the core sample whereas the upper end 380 exposes the circular (330 and 340) and radial (350) array of channels interconnected with center passageway 360 with formed holes 300, 310, and 320 disposed therein. The perforated base plate 100, in the preferred embodiment, is made from No. 17-4PH stainless steel for non-corrosive gas service, or from Hastelloy-C for corrosive liquid service, and press fittingly engages the corresponding cavity in the end plug 150 or in the piston 70 as shown in FIG. 1. While the channels are shown having a rectangular cross-section, it is to be expressly understood that a semi-circular cross-section or other design could also be used.

This specific arrangement of holes and channels aids in the uniform distribution of gas into and out from the core sample and provides mechanical support at the high overburden stresses being applied to the core sample when porosity and permeability tests are conducted so that the ends of the core samples are not damaged. In particular, the present invention minimizes damage to the core ends by providing a flat surface with the forty-eight holes formed therein. The flat surface minimizes deformation of the core ends while the holes permit the uniform injection of gas over the entire end of the plug. If the ends of the core samples are damaged, an error in the test, such as permeability and porosity, could result.

It is to be expressly understood that under the teachings of the present invention while two channels 330 and 340 are shown in the preferred embodiment, at least one circular channel is required to provide fluid interconnection between the radial channels (350). Furthermore while three circular arrays of holes 300, 310, and 320 are shown this could well be a plurality of such arrays more or less than three. Likewise, while eight radial channels are shown in the preferred embodiment, this also could be more or less.

In one embodiment, the plate of the present invention is approximately one inch in diameter, one-tenth of an inch thick. Each circular hole is approximately 0.06 inch in diameter and each channel is 0.06 inch wide and 0.045 inches deep.

While a preferred embodiment of the present invention has been disclosed it is to be expressly understood that changes and modifications could be made thereto without departing from the scope of the invention as set forth in the following claims.

I claim:

1. An improved perforated end plug circular plate having one surface abutting at least one end of a core sample during testing of the core sample, said perforated end plug plate being in fluid communication with a fluid for delivering said fluid into said at least one end, said improved end plug plate comprising said circular plate having at least one circular channel (330, 340) formed on the surface (380) opposing said abutting surface (370) located between the center and outer circumference of said plate; a plurality of radial channels formed on said opposing surface (380), in fluid communication with said at least one circular channel (330, 340), and emanating from a formed circular cavity (360) located in the center of said plate outwardly to said circumference; and at least one circular array (300, 310, 320) of holes formed in said abutting surface (370) and located in said at least one circular channel (330, 340) and said plurality of radial channels (380), so that said cavity (360) is in fluid communication with said fluid for extending said fluid through said radial channels into said at least one circular channel (330, 340), through said at least one circular array of holes (300, 310, 320) and into said core sample.

2. The improved end plug plate of claim 1 wherein said formed circular and radial channels (330, 340, 380) have a rectangular cross-section.

3. The improved end plug plate of claim 1 wherein said formed holes (300, 310, 320) are circular.

4. The improved end plug plate of claim 1 wherein three circular arrays of holes (300, 310, 320) are formed in said abutting surface (370).

5. The improved end plug of claim 4 wherein the outer two circular arrays of holes (300, 310) are each located in a corresponding circular channel (330, 340) and wherein each hole of the innermost circular array of holes (320) is located in one of said plurality of radial channels.

6. An improved perforated end plug circular plate having one surface abutting at least one end of a core sample during testing of said core sample, said perforated end plug plate being in fluid communication with a fluid for delivering said fluid into said at least one end, said improved end plug plate comprising said circular plate having two circular channels (330, 340) formed on the surface (380) opposing said abutting surface (370) located between the center and outer circumference of said plate; a plurality of radial channels formed on said opposing surface (380), in fluid communication with said circular channels (330, 340), and emanating from a formed circular cavity (360) located in the center of said plate outwardly to said circumference; and three circular arrays (300, 310, 320) of holes formed in said abutting surface (370) and located in said circular channels (330, 340) and said plurality of radial channels, so that said cavity (360) is in fluid communication with said fluid for extending said fluid through said radial channels into said circular channels (330, 340), through said circular arrays of holes (300, 310, 320) and into said core sample.

* * * * *